US010531963B2

(12) United States Patent
Zakelj et al.

(10) Patent No.: US 10,531,963 B2
(45) Date of Patent: Jan. 14, 2020

(54) INTERBODY SPINE IMPLANT

(71) Applicant: Life Spine, Inc., Huntley, IL (US)

(72) Inventors: Paul C. Zakelj, Chicago, IL (US);
Adam Goon, Denver, CO (US);
Madeline C. Wolters, St. Charles, IL (US)

(73) Assignee: Life Spine, Inc, Huntley, IL (US)

( * ) Notice: Subject to any disclaimer, the term of this patent is extended or adjusted under 35 U.S.C. 154(b) by 100 days.

(21) Appl. No.: 15/947,822

(22) Filed: Apr. 8, 2018

(65) Prior Publication Data
US 2018/0289500 A1    Oct. 11, 2018

Related U.S. Application Data

(60) Provisional application No. 62/483,625, filed on Apr. 10, 2017.

(51) Int. Cl.
*A61F 2/44* (2006.01)
*A61F 2/30* (2006.01)
*A61B 17/86* (2006.01)

(52) U.S. Cl.
CPC .......... *A61F 2/447* (2013.01); *A61B 17/8625* (2013.01); *A61F 2/30771* (2013.01); *A61F 2002/3079* (2013.01); *A61F 2002/30135* (2013.01); *A61F 2002/30604* (2013.01); *A61F 2002/30827* (2013.01)

(58) Field of Classification Search
CPC ........ A61F 2/4455; A61F 2/447; A61F 2/446; A61F 2/4465; A61F 2/4611; A61B 17/7059
USPC ...................................... 623/17.16
See application file for complete search history.

(56) References Cited

U.S. PATENT DOCUMENTS

| 2013/0218276 A1* | 8/2013 | Fiechter | A61F 2/4455 |
| | | | 623/17.16 |
| 2014/0039623 A1* | 2/2014 | Iott | A61F 2/30744 |
| | | | 623/17.16 |
| 2014/0142705 A1* | 5/2014 | Duffield | A61F 2/442 |
| | | | 623/17.16 |
| 2016/0089249 A1* | 3/2016 | McDonough | A61B 17/1757 |
| | | | 623/17.16 |

* cited by examiner

*Primary Examiner* — Si Ming Ku
(74) *Attorney, Agent, or Firm* — Foley & Lardner LLP

(57) ABSTRACT

An interbody spine implant has a PEEK body/cage and removable front, the body with bone screw holes of a diameter smaller than a greatest diameter of an associated bone screw such that received bone screws cut into the PEEK thus locking the bone screws to the body. A major diameter of a bone screw increases towards the head of the screw to cause interference between the PEEK body and the screw. This aids in preventing the screw from backing out of the body. Bone screw holes are angled to project the bone screw from either the top or the bottom of the body for receipt in upper and lower vertebral bone. Preferably, but not necessarily, the direction of the bone screw bores are staggered from one lateral side to another lateral side of the body.

17 Claims, 5 Drawing Sheets

INTERBODY SPINE IMPLANT

CROSS-REFERENCE TO RELATED APPLICATIONS

This U.S. non-provisional patent application claims the benefit of and/or priority under 35 U.S.C. § 119(e) to U.S. provisional patent application Ser. No. 62/483,625 filed Apr. 10, 2017 titled "Spine Implant," the entire contents of which is specifically incorporated herein by reference.

FIELD OF THE INVENTION

The present invention relates to orthopedic implants for the spine and, particularly, to interbody implants for the spine.

BACKGROUND OF THE INVENTION

Many people contend with spine issues as a result of age, disease, and trauma, as well as congenital and acquired complications and conditions. While some of these issues can be alleviated without surgery, other issues necessitate surgery. Issues with the spine such as decompression and stabilization can be addressed with spine implants. One type of spine implant is placed within the interbody or disc space once disc tissue has been removed. The interbody implant is typically secured to one or both of the upper and lower vertebrae. Bone graft may or may not be used with the interbody implant for vertebral fusion, which stops all movement between vertebrae.

The purpose of an interbody implant is to maintain disc height between vertebrae to help prevent nerve compression, restore and preserve the natural alignment of the spine, and promote spinal fusion. In some cases the interbody implant may be a holder or carrier for fusion/graft material. In other cases the interbody implant may stand alone to provide structural stability.

SUMMARY OF THE INVENTION

An interbody spine implant has a PEEK body or cage and removable front, the body with bone screw holes of a diameter smaller than a greatest diameter of an associated bone screw such that received bone screws cut into the PEEK thus locking the bone screws to the implant, the front holding the head of the screw. A major diameter of a bone screw increases towards the head of the screw to cause interference between the PEEK body and the screw. This aids in preventing the screw from backing out of the body. Bone screw holes are angled to project the bone screw from either the top or the bottom of the PEEK body for receipt in upper and lower vertebral bone. Preferably, but not necessarily, the direction of the bone screw bores are staggered from one lateral side to another lateral side of the body.

The interbody spine implant has four bone screw bores, two of which extend and angle from the front to the upper side of the body, and two of which extend from the front to the lower side of the body. More or less bone screw bores may be provided. Preferably, but not necessarily, the direction of the bone screw bores are staggered from one lateral side to another lateral side of the body.

Preferably, but not necessarily, the upper and lower surfaces of the body include serrations, teeth or the like. The serrations, teeth or the like preferably, but not necessarily, are directional.

Preferably, but not necessarily, the body is wedge shaped with the end supporting the removable front wider and taller than an opposite, insertion end of the body.

Further aspects of the present invention will become apparent from consideration of the figures and the following description of the invention. A person skilled in the art will realize that other forms of the invention are possible and that the details of the invention can be modified in a number of respects without departing from the inventive concept. The following figures and description are to be regarded as illustrative in nature and not restrictive.

BRIEF DESCRIPTION OF THE DRAWINGS

The features of the invention will be better understood by reference to the accompanying drawings which illustrate a form of the present invention, wherein.

It should be appreciated that dimensions of the components, structures, and features of the present interbody spine implant can be altered as desired.

DETAILED DESCRIPTION OF THE INVENTION

Figure 1:
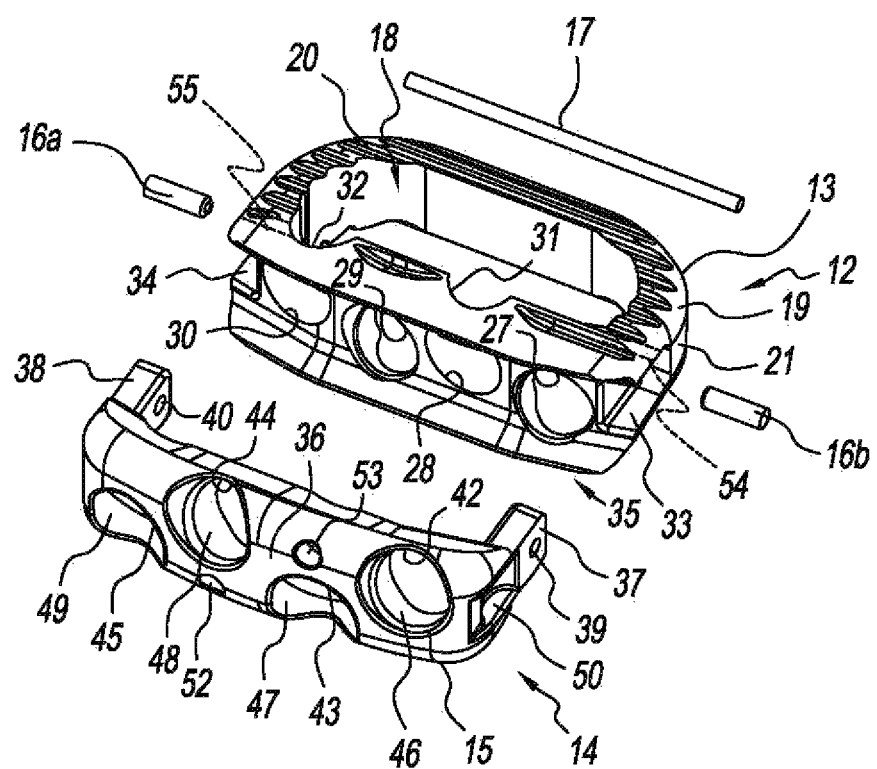
FIG. 1 is an exploded view of an interbody spine implant made in accordance with the present principles.
Figure 2:
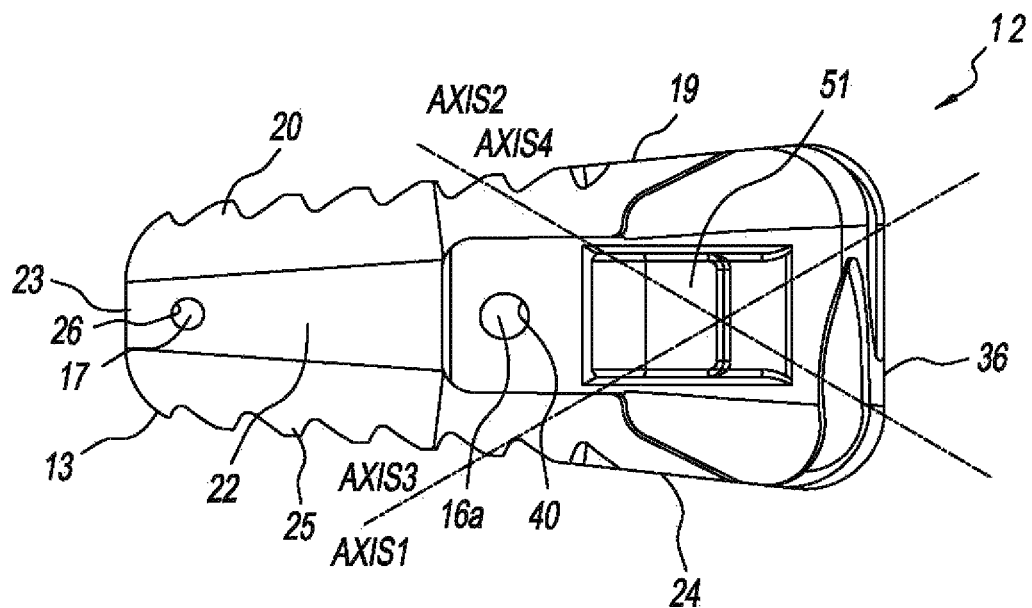
FIG. 2 is a side plan view of the interbody spine implant of FIG. 1, assembled.
Figure 3:
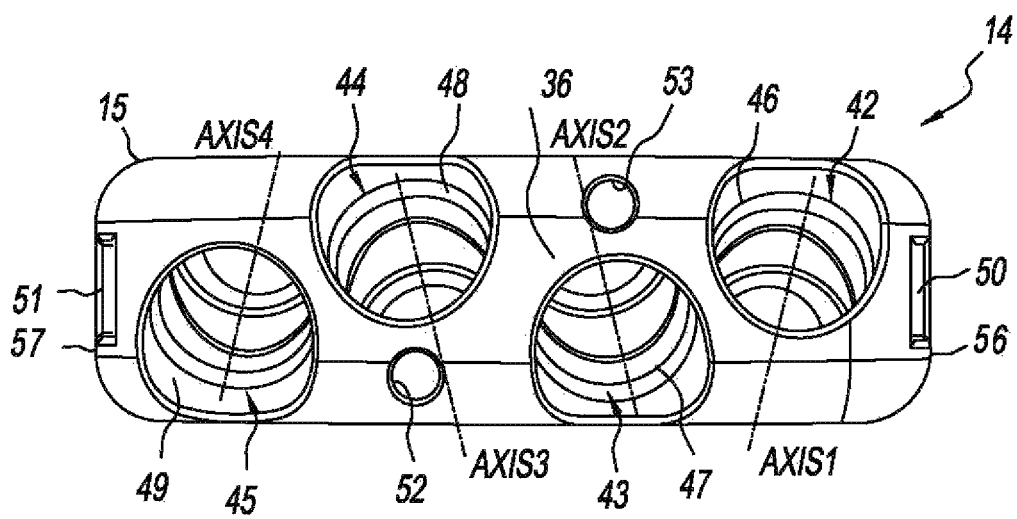
FIG. 3 is a front plan view of the interbody spine implant of FIG. 1, assembled.
Figure 4:
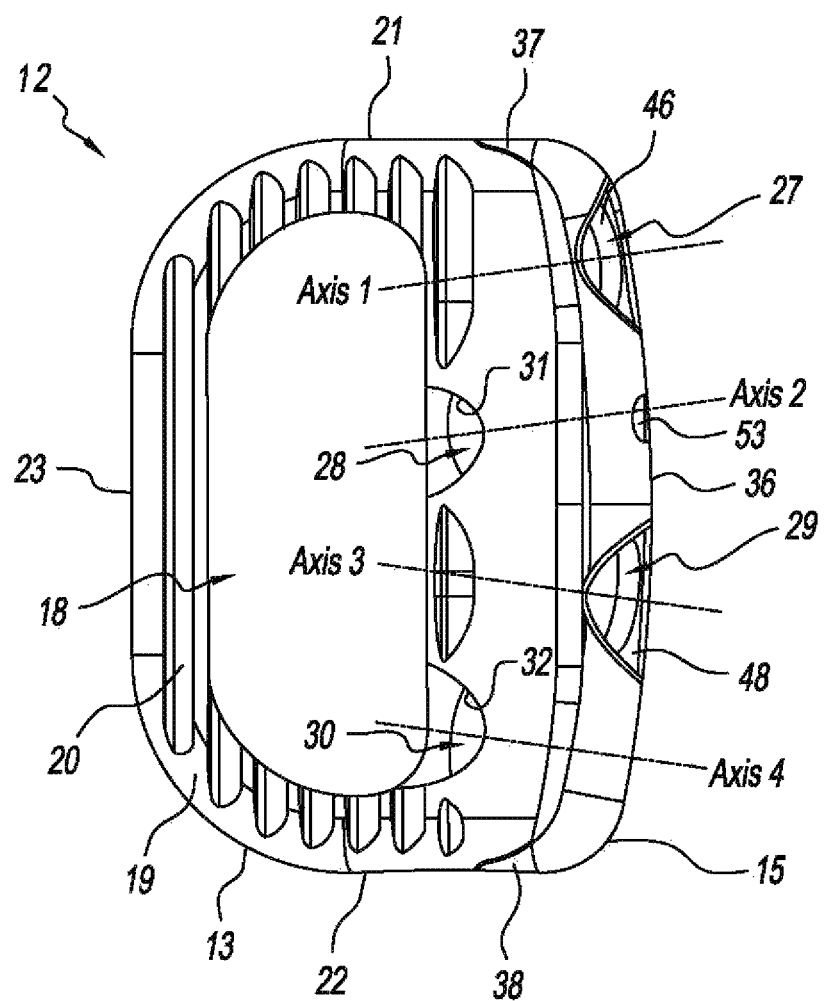
FIG. 4 is a top plan view of the interbody spine implant of FIG. 1, assembled.
Figure 5:
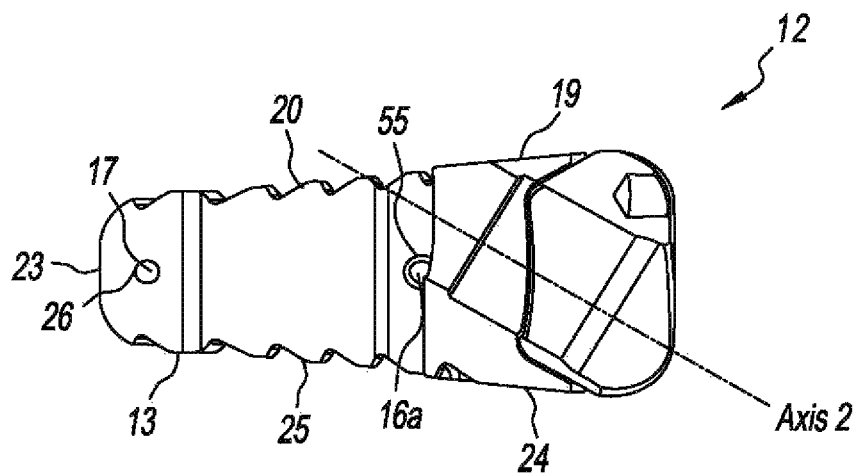
FIG. 5 is a side sectional view of the interbody spine implant of FIG. 1, assembled.
Figure 6:
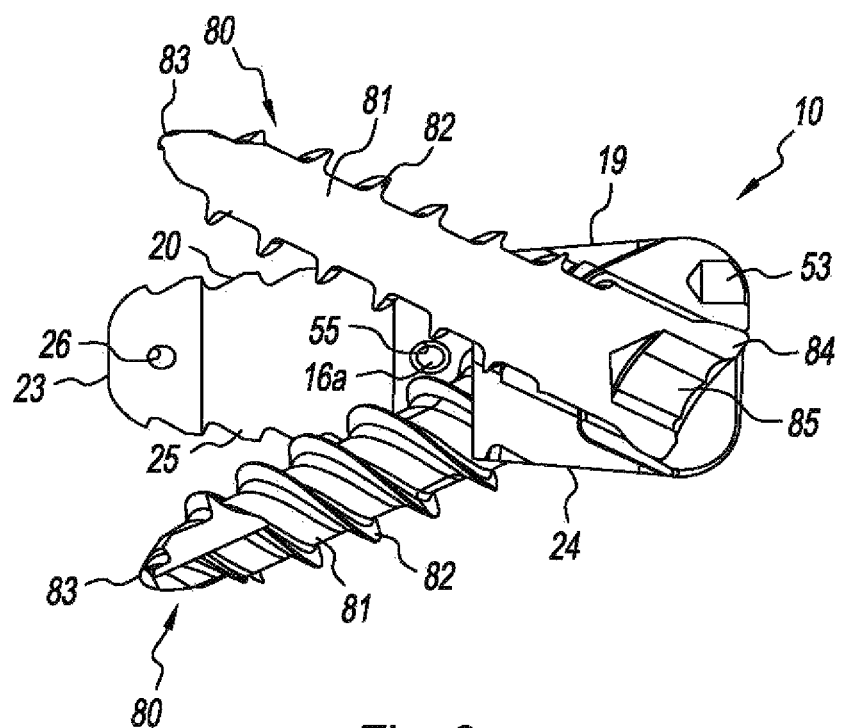
FIG. 6 is a side sectional view of the interbody spine implant of FIG. 1, assembled, with bone screws installed.
Figure 7:
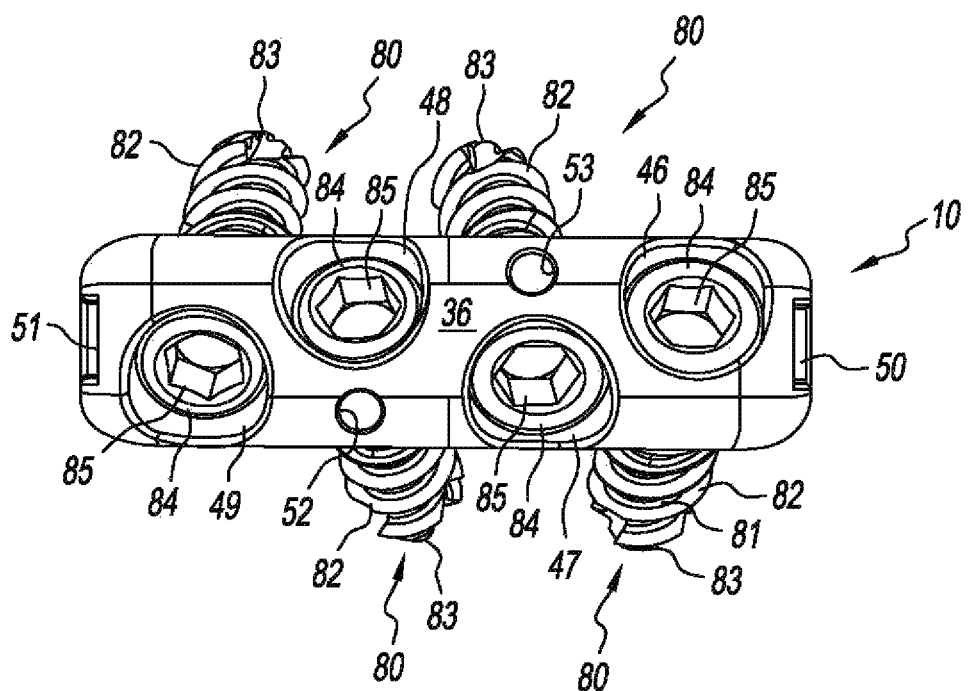
FIG. 7 is a front plan view of the interbody spine implant of FIG. 1, assembled, with bone screws installed.
Figure 8:
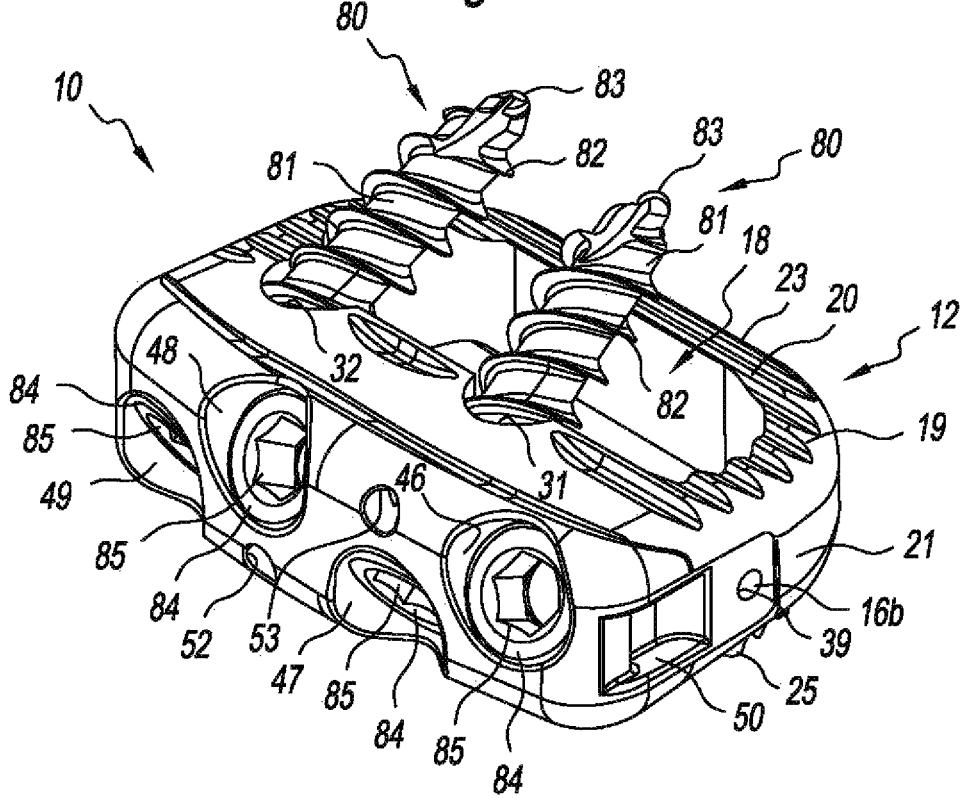
FIG. 8 is an isometric front top view of the interbody spine implant of FIG. 1, assembled, with bone screws installed.

Referring to FIGS. 1-8, there is shown an interbody spine implant, generally designated 12, fashioned in accordance with the present principles, the interbody spine implant 12 with bone screws 80 provides an interbody spine implant system 10.

Each bone screw 80 is characterized by a shaft 81 with external threading 82 with a tip 83 at one end of the shaft 81 and a head 84 at the other end of the shaft 81. The threading 82 of the shaft 81 is configured to engage bone, and particularly vertebral bone. The head 84 is generally cylindrical and has a socket 85 in its upper surface that is configured to receive a like configured installation tool (not shown). The socket 85 may be configured as a hexalobe, hexagon, or other shape, the installation tool therefore having a like shaped configuration. Below the head 84 is a neck having a diameter larger than the diameter of the threaded shaft 81, the larger diameter preferably, but not necessarily, the greatest diameter of the bone screw. In general, the diameter of the bone screw increases from the tip 83 to the head 84. Axially below the neck is an inwardly angled portion that then tapers down to the decreasing diameter shaft 81. The bone screw 80 is formed of a suitable biocompatible material such as, but not limited to, titanium, stainless steel, or an alloy of either. The bone screw 80 shown and described herein interacts with the configuration of the implant 12 as described herein.

The interbody spine implant 12 is characterized by a body 13 preferably, but not necessarily formed of PEEK, or other similar bio-compatible materials. The body 13 is fashioned generally as a wedge having an upper side 19, a lower side 24 opposite to the upper side 19, a first lateral side 21, a second lateral side 22 that is opposite to the first lateral side 21, a first end (nose) 23, and a second end (rear) 35 opposite to the first end 23, the nomenclature first, second, upper and lower being arbitrary. Being wedge-shaped, the second end 35 is taller and slightly wider than the first end 23 (see, e.g. FIG. 4). The body 13 further includes a central opening 18. The opening 18 provides a cavity for receiving fusion material such as, but not limited to, bone graft. The body 13 has a bore 26 proximate the rear end 23 and extending from the first lateral side 21 to the second lateral side 22. A radiographic marker 17 (here in the form of a rod) may be received in the bore 26 to indicate via x-ray, the posterior extent of the body/cage 13.

The upper side 19 of the body 13 has serrations, teeth, grooves or the like (serrations) 20 extending from the first lateral side 21 to the second lateral side 22 and spaced generally from the first end 23 to the second end 35. The lower side 24 likewise has serrations, teeth, grooves or the like (serrations) 25 extending from the first lateral side 21 to the second lateral side 22 and spaced generally from the first end 23 to the second end. The serrations 20, 25 allow the first end 23 and thus the interbody spine implant 12 to be easily inserted into a spinal cavity but resist extrication of the interbody spine implant 12 from the spinal cavity.

The second end (rear) 35, the first lateral side 56, and the second lateral side 57 are configured as described to receive a removable front 14 that is preferably, but not necessarily, formed of PEEK, understanding that other materials may be used. The front 14 has a body 15 as shown, defining a face 36, a first leg 37 extending generally perpendicular to and at a rear of a first lateral side 56 of the face 36, and a second leg 38 extending generally perpendicular to and at a rear of a second lateral side 57 of the face 36, the nomenclature first and second being arbitrary here and throughout. The first leg 37 has a bore 39 extending therethrough that is sized to receive a pin 16b that attaches the first leg 37 to the implant body 13 as shown and described below. The second leg 38 has a bore 40 extending therethrough that is sized to receive a pin 16a that attaches the second leg 38 to the implant body 13 as shown and described below.

A first notch 50 is disposed at the first lateral side 56 and a second notch 51 at the second lateral side 57, the notches 50, 51 allowing the reception of an installation tool (not shown). The implant 12 is structured to accept a plurality of the bone screws 80 for attaching to and stabilizing the implant 12 relative to upper and lower vertebrae/vertebral bodies (not shown). In the embodiment shown, the implant 12 is structured to accept four (4) bone screws 80. The front 14 thus has four (4) angled bores 42, 43, 44, 45 (see e.g. FIGS. 2, 4, 5 for the axes of the angles of the bores, Axis 1 of the bore 42, Axis 2 of the bore 43, Axis 3 of the bore 44, and Axis 4 of the bore 45) with open bottoms to accept four (4) bone screws 80 and defining four (4) angled pockets 46, 46, 46, 49 all sized to allow the threaded shaft 81 of the bone screw 80 to extend through the bore and out of its open bottom but provide a seat for the head 84 of the bone screw 80 by the pocket (see, e.g., FIG. 3), to stop the bone screw from advancing through the body 15. The front 14 also includes two small holes 52, 53 for receipt of a radiographic marker (not shown), and/or to aid in implantation.

The four (4) bores/pockets 42/46, 43/47, 44/48, 45/49 are spaced along the face 14 from the first lateral side 56 to the second lateral side 57 in a staggered pattern relative to a centerline of the front 36 as taken from the second lateral side 57 to the first lateral side 56. The first and third pockets 22, 24 are angled such that the received bone screw 80 extends from the lower side 24 of the body 13, while the second and fourth pockets 23, 25 are angled such that the received bone screw 80 extends from the upper side 19 of the body 13. The bone screws 80 extending from the lower side 24 of the body 13 are received in a lower vertebrae (not seen) while the bone screws 80 extending from the upper side 19 of the body 13 are received in an upper vertebrae (not seen). The upper portion of the body 13 proximate the front 35 has a first cutout 31 to allow the shaft 81 of the bone screw 80 to properly extend from the angled bore 28 of the body 13 and out of the opening 18 of the body 13, and a second cutout 32 to allow the shaft 81 of the bone screw 80 to properly extend from the angled bore 30 of the body 13 and out of the opening 18 of the body 13. The lower portion of the body 13 proximate the front 35 has a third cutout (not seen) to allow the shaft 81 of the bone screw 80 to properly extend from the angled bore 27 of the body 13 and out of the opening 18 of the body 13, and a fourth cutout (not seen) to allow the shaft 81 of the bone screw 80 to properly extend from the angled bore 29 of the body 13 and out of the opening 18 of the body 13, the nomenclature third and fourth being arbitrary. It should be appreciated that the present implant 10 may utilize more or less bone screws, and in a different staggered pattern for attachment to an upper and lower vertebrae/vertebral bone.

The implant body 13 has a bore 27, 28, 29, 30 for receiving each bone screw 80 that extends from each bore 42, 43, 44, 45 of the front 14. Each bore is sized smaller than the greatest or major diameter of the bone screw 80 (i.e. neck) such that the threading/neck of the bone screw cuts into the PEEK when the bone screw is fully seated, causing interference between the bone screw and PEEK body to lock the bone screw in place and/or at least inhibit, but preferably prevent, bone screw back out.

The body 13 further includes a first notch 50 disposed at the first lateral side 56 of the body and a second notch 51 at the second lateral side 57 of the body 13. The notches 50, 51 are sized to allow an installation instrument/tool (not seen) to grasp the body 13 and/or receive respective first and second legs 37, 38 of the face. While not seen, a bore is provided in the notch 50 to allow receipt of a portion of the pin 16b, while a bore is provided in the notch 51 to allow receipt of a portion of the pin 18a, in order to retain the face 14 onto the body 13.

It should be appreciated that dimensions of the components, structures, and/or features of the present interbody spine implant may be altered as desired within the scope of the present disclosure.

What is claimed is:

1. A spine implant comprising:
a body defining a front end, a back end opposite the front end, a first lateral end, a second lateral end opposite the first lateral end, an upper side, a lower side opposite the upper side, a first notch in the first lateral end, a second notch in the second lateral end, a first notch bore in the first notch, a second notch bore in the second notch, and a cavity situated between the upper and lower sides, the first and second lateral ends, and the front and back ends, and having a plurality of bone screw bores extending from the front end into the cavity, each one of the plurality of bone screw bores having a first diameter, and angled to project a threaded shaft of a bone screw into the cavity from either the upper side or the lower side;

a first attachment pin;

a second attachment pin;

a front having a face, a first lateral end, a second lateral end opposite the first lateral end, a first leg extending transverse from the first lateral end and configured for receipt in the first notch of the body, a second leg extending transverse from the second lateral end and configured for receipt in the second notch of the body, a first leg bore extending through the first leg and sized to receive the first attachment pin, a second leg bore extending through the second leg and sized to receive the second attachment pin, the front removably attached to the body through receipt of the first leg in the first notch of the body and receipt of the first attachment pin into the first leg bore and the first notch bore, and the second leg in the second notch of the body and receipt of the second attachment pin into the second leg bore and the second notch bore, the front further having a plurality of bone screw holes of the first diameter and corresponding in number, placement and angle of the plurality of bone screw bores of the body; and a bone screw for each one of the plurality of bone screw bores of the body, each bone screw having a head, a neck extending axially from the head, and a threaded shaft extending axially from the neck, the neck having a second diameter that is less than the first diameter;

wherein receipt of a bone screw into one of the plurality of bone screw bores of the body causes the neck to cut into the body, thereby retaining the bone screw by interference.

2. The spine implant of claim 1, wherein the body and the removable front comprise PEEK.

3. The spine implant of claim 2, further comprising:
a rod bore in the body and extending from the first lateral end to the second lateral end proximate the back; and
a radiographic rod disposed in the rod bore.

4. The spine implant of claim 3, wherein the removable front has a first channel in the first lateral end, and a second channel in the second lateral end, the first and second channels configured for receipt of an installation tool.

5. The spine implant of claim 1, wherein each one of the plurality of bone screw bores has an axis that is skewed relative to an axis of an adjacent bone screw bore.

6. The spine implant of claim 5, wherein the plurality of bone screw bores comprises four.

7. The spine implant of claim 6, wherein a first pair of bone screw bores of the four bone screw bores is defined having co-axial axes, and a second pair of bone screw bores of the four bone screw bores is defined having co-axial axes and that are skewed relative to the co-axial axes of the first pair of bone screw bores.

8. The spine implant of claim 7, wherein the first pair of bone screw bores have axes that angle downwardly, and the second pair of bone screw bores have axes that angle upwardly.

9. The spine implant of claim 7, wherein the first pair of bone screw bores extend from an upper area of the front end, and the second pair of bone screw bores extend from a lower area of the front end.

10. An interbody spine implant comprising:
a body having a front end, a back end opposite the front end, a first lateral end, a second lateral end opposite the first lateral end, an upper side, a lower side opposite the upper side, a first notch in the first lateral end adjacent the front end, a second notch in the second lateral end adjacent the front end, a first notch bore in the first notch, a second notch bore in the second notch, a cavity situated between the upper and lower sides, the first and second lateral ends, and the front and back ends, and four bone screw bores extending from the front end and into the cavity, each one of the four bone screw bores having a first diameter and angled to project a threaded shaft of a bone screw into the cavity from either the upper side or the lower side;

a first pin;

a second pin;

a front having a face, a first lateral end, a second lateral end opposite the first lateral end, a first leg extending transverse from the first lateral end and configured for receipt in the first notch of the body, a second leg extending transverse from the second lateral end and configured for receipt in the second notch of the body, a first leg bore extending through the first leg and sized to receive the first pin, a second leg bore extending through the second leg and sized to receive the second pin, the front attached to the body through receipt of the first leg in the first notch of the body and receipt of the first pin into the first leg bore and the first notch bore, and the second leg in the second notch of the body and receipt of the second pin into the second leg bore and the second notch bore; and a bone screw for each one of the four bone screw bores of the body, each bone screw having a head, a neck extending axially from the head, and a threaded shaft extending axially from the neck, the neck having a second diameter that is less than the first diameter;

wherein receipt of a bone screw into one of the four bone screw bores of the body causes the neck to cut into the body, thereby retaining the bone screw by interference.

11. The interbody spine implant of claim 10, wherein the body and the front comprise PEEK.

12. The interbody spine implant of claim 11, further comprising:
a rod bore in the body and extending from the first lateral end to the second lateral end proximate the back; and
a radiographic rod disposed in the rod bore.

13. The interbody spine implant of claim 12, wherein the front has a first channel in the first lateral end, and a second channel in the second lateral end, the first and second channels configured for receipt of an installation tool.

14. The interbody spine implant of claim 10, wherein each one of the four bone screw bores has an axis that is skewed relative to an axis of an adjacent bone screw bore.

15. The interbody spine implant of claim 14, wherein a first pair of bone screw bores of the four bone screw bores is defined having co-axial axes, and a second pair of bone screw bores of the four bone screw bores is defined having co-axial axes and that are skewed relative to the co-axial axes of the first pair of bone screw bores.

16. The interbody spine implant of claim 15, wherein the first pair of bone screw bores have axes that angle downwardly, and the second pair of bone screw bores have axes that angle upwardly.

17. The interbody spine implant of claim 15, wherein the first pair of bone screw bores extend from an upper area of the front end, and the second pair of bone screw bores extend from a lower area of the front end.

* * * * *